United States Patent
Qu et al.

(10) Patent No.: US 9,554,911 B2
(45) Date of Patent: Jan. 31, 2017

(54) ARTIFICIAL KNEE JOINT

(71) Applicant: Beijing Naton Technology Group Co., Ltd., Beijing (CN)

(72) Inventors: Tiebing Qu, Beijing (CN); Cheng-kung Cheng, Beijing (CN); Dayong Song, Beijing (CN); Lili Hou, Beijing (CN)

(73) Assignee: BEIJING NATON TECHNOLOGY GROUP CO., LTD, Beijing (CN)

( * ) Notice: Subject to any disclaimer, the term of this patent is extended or adjusted under 35 U.S.C. 154(b) by 70 days.

(21) Appl. No.: 14/361,172

(22) PCT Filed: Nov. 28, 2012

(86) PCT No.: PCT/CN2012/085436
§ 371 (c)(1),
(2) Date: May 28, 2014

(87) PCT Pub. No.: WO2013/078994
PCT Pub. Date: Jun. 6, 2013

(65) Prior Publication Data
US 2015/0134067 A1    May 14, 2015

(30) Foreign Application Priority Data
Nov. 28, 2011  (CN) .......................... 2011 1 0385645

(51) Int. Cl.
*A61F 2/38* (2006.01)
(52) U.S. Cl.
CPC ........... *A61F 2/3836* (2013.01); *A61F 2/3886* (2013.01)
(58) Field of Classification Search
CPC .................................................. A61F 2/3886
(Continued)

(56) References Cited

U.S. PATENT DOCUMENTS 5,549,686 A    8/1996  Johnson et al.
6,123,729 A    9/2000  Insall et al.
(Continued)

FOREIGN PATENT DOCUMENTS

BE    WO 9930649 A1 *  6/1999  .......... A61F 2/3868
CN    102006840 A       4/2011
(Continued)

OTHER PUBLICATIONS

Supplementary European Search Report of EP 12853451 dated Apr. 16, 2015.
(Continued)

*Primary Examiner* — David H. Willse
*Assistant Examiner* — Javier Blanco
(74) *Attorney, Agent, or Firm* — Amster, Rothstein & Ebenstein LLP

(57) ABSTRACT

An artificial knee joint includes a femoral component (1) and a tibial component (2). The femoral component (1) includes an intercondylar box (11). A cam (12) is provided on posterior of the intercondylar box (11). The tibial component (2) includes a medial condyle bearing surface (21) and a lateral condyle bearing surface (22) arranged on right and left side respectively. A post (23) is provided between the medial condyle bearing surface (21) and the lateral condyle bearing surface (22). The post (23) is adapted to the intercondylar box (11). The post (23) has a first arc surface (231) on the lateral side of posterior surface. The post (23) has a second arc surface (232) on the posterior surface and on the medial side of the first arc surface (231). A third arc surface (121) and a forth surface (122), cooperating with the first arc surface (231) and the second arc surface (232), are provided on the cam (12) accordingly. The first arc surface (231) can cooperate with the third arc surface (121) so as to guide the femur to rotate laterally with respect to the tibia.

(Continued)

The second arc surface (232) can cooperate with the forth surface (122) so as to resist the femur to rotate laterally with respect to the tibia. The artificial knee joint can simulate accurately the flexion-extension action of the knee joint, and is safe and reliable.

5 Claims, 5 Drawing Sheets

(58) Field of Classification Search
USPC .............. 623/20.15, 20.21, 20.27, 20.31
See application file for complete search history.

(56) References Cited

U.S. PATENT DOCUMENTS

| 2005/0143832 | A1* | 6/2005 | Carson | A61F 2/3886 |
| | | | | 623/20.28 |
| 2005/0209701 | A1 | 9/2005 | Suguro et al. | |
| 2009/0319049 | A1 | 12/2009 | Shah et al. | |
| 2010/0016979 | A1* | 1/2010 | Wyss | A61F 2/3886 |
| | | | | 623/20.27 |
| 2010/0234961 | A1* | 9/2010 | Otto | A61F 2/3836 |
| | | | | 623/20.29 |
| 2012/0089234 | A1* | 4/2012 | Mouillet | A61F 2/3886 |
| | | | | 623/20.21 |
| 2012/0143342 | A1* | 6/2012 | Mihalko | A61F 2/3886 |
| | | | | 623/20.27 |

FOREIGN PATENT DOCUMENTS

| CN | 102076283 A | 5/2011 |
| CN | 202335945 U | 7/2012 |
| EP | 1440675 A1 | 7/2004 |

OTHER PUBLICATIONS

International Search Report mailed Feb. 14, 2013 for PCT Application No. PCT/CN2012/085436, filed Nov. 28, 2012.

* cited by examiner

ARTIFICIAL KNEE JOINT

TECHNICAL FIELD

The present disclosure relates to a prosthesis applied to the human body, and in particular to a prosthesis having a structural function of a knee joint.

BACKGROUND

Currently, the normal walking and flexion and extension of knee joints of many patients cannot be achieved due to the damage of muscles and cartilaginous tissues. In this case, prostheses are required to be implanted to replace the knee joints to help the patients to stand, walk and flex and extend normally again. Although the artificial knee joints have been widely applied, the traditional artificial knee joint is not meticulous enough when simulating the action of a natural knee and hence the human body cannot act in position smoothly when using the prosthesis and often cannot act properly. Particularly when the flexion of the knee joint is simulated, the traditional artificial knee joint only pays attention to the flexion and extension between a femur and a tibia of the knee joint during the flexion but ignores the external rotation of the femur relative to the tibia during the flexion. Therefore, it is substantively very difficult to achieve proper flexion in position, and the prosthesis can even be damaged as the action does not comply with the physiological characteristic of the human body; moreover, even the femur and the tibia of the patient can be damaged as well, and hence the patient's condition can be worse.

However, the external rotation of the knee of the human body during the flexion must be smooth and the movement range cannot be too large, or else the patient would be hurt. At present, although the problem has been considered b those skilled in the art, an actual means for solving the problem cannot be put forward. In the process of the simulation of the external rotation of the femur relative to the tibia, not only the action must be smooth but also further external rotation must be stopped in time. If the external rotation cannot be stopped in time, the problem of dislocation wilt be caused and even the personal safety will be affected. Therefore, as no effective means can be provided so far, the prosthesis designer is afraid of this for exclusion of liability.

SUMMARY

An objective of the present disclosure is to solve the problem of the prior art and provide an artificial knee joint, in which the structure is simple and the knee joint can not only perform the flexion motion but also achieve the external rotation of a femur relative to a tibia during the flexion and extension of the knee joint.

In order to achieve the objective, the present disclosure adopts the following technical solutions:

An artificial knee joint comprises a femoral component and a tibial component cooperating with each other and adapted to a femur and a tibia, respectively; the femoral component includes an intercondylar box; a cam is disposed at the posterior of the intercondylar box; the tibial component includes a medial condyle supporting surface and a lateral condyle supporting surface; a post is disposed between the medial condyle supporting surface and the lateral condyle supporting surface and cooperates with the intercondylar box; a first arc surface is formed on a posterior-lateral surface of the post; a second arc surface is formed on the posterior-medial surface of the post; the cam correspondingly comprises a third arc surface and a fourth arc surface cooperating with the first arc surface and the second arc surface, respectively; the first arc surface can cooperate with the third arc surface to guide the external rotation of the femur relative to the tibia; and the second arc surface can cooperate with the fourth arc surface to constrain the external rotation of the femur relative to the tibia.

Moreover, in view of the cross section, the curvature of the first arc surface is the same as that of the third arc surface; the curvature of the second arc surface is the same as that of the fourth arc surface; and the curvature of the second arc surface and the fourth arc surface is smaller than that of the first arc surface and the third arc surface.

Moreover, the first arc surface, the second arc surface, the third arc surface and the fourth arc surface are all circular surfaces.

Moreover, the radius of the first arc surface and the third arc surface is 3 to 10 mm; and the radius of the second arc surface and the fourth arc surface is 30 to 50 mm.

Moreover, in the cross section of the tibial component, a line, which connects the center of the first arc surface and the intersection of the first and second arc surfaces, extends at an angle ranging about 5 to 20 degrees relative to the posterior-anterior axis of the tibia.

Moreover, the center of the post deviates from the center of the tibial component, and the post is disposed on a posterior-lateral portion of the tibial component, towards to the lateral condyle supporting surface.

Moreover, both the post and the cam are structurally asymmetrical.

Moreover, the posterior surface of the post rotates externally relative to a vertical plane of the bottom of the tibial component.

Moreover, the largest diameters of the two ends of the cam are equal to each other Moreover, part of the anterior portion is cut in the anterior inferior direction from the post to form a lower anterior surface on the post. An anterior surface of the post is a circular surface, and the post is in the shape of a thumb with radian on the whole in side view.

Compared with the prior art, in the present disclosure, the first arc surface on the post and the third arc surface on the cam cooperate with each other to conveniently guide smooth external rotation of the femur relative to the tibia; the second arc surface on the post and the fourth arc surface on the cam cooperate with each other to gradually constrain the external rotation of the femur relative to the tibia; and when the second arc surface and the fourth arc surface make fun contact with each other, the external rotation of the femur relative to the tibia can be completely constrained. The artificial knee joint provided by the present disclosure adopts an actual means to accurately simulate the flexion and extension of the knee joint, is safe and reliable, can further improve the usage level of the artificial knee joint, and satisfies higher requirements of patients, meanwhile, the product according to the disclosure has a higher market value.

DETAILED DESCRIPTION

Detailed description will be given below to the preferred embodiments which illustrate the characteristics and advantages of the present disclosure. It should be understood that various variations could be made to the present disclosure on the basis of different embodiments without departing from the scope of the present disclosure; and the description and accompanying drawings therein are only for illustration in essence and not intended to limit the present disclosure.

In the present disclosure, the "anterior" direction and the "posterior" direction referred to herein are consistent with the direction of the human body after the artificial knee joint is implanted into the human body. Description will be given to the present disclosure by taking a left artificial knee joint as an example.

Figure 1:
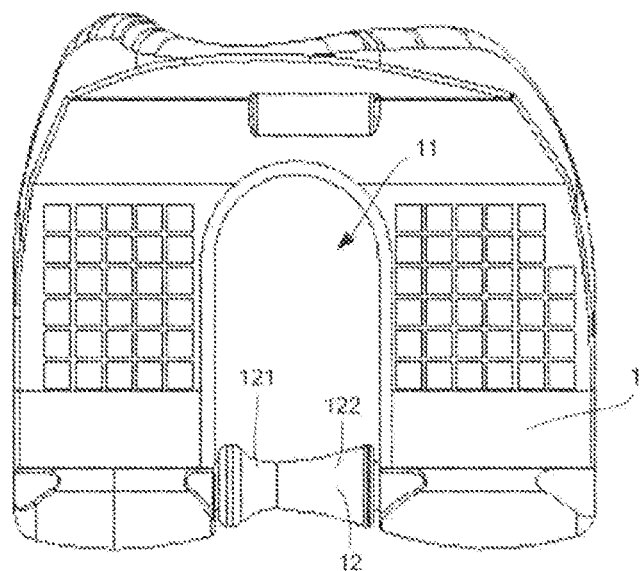
FIG. 1 is a schematic structural view of a femoral component in an artificial knee joint provided by the present disclosure.
Figure 2:
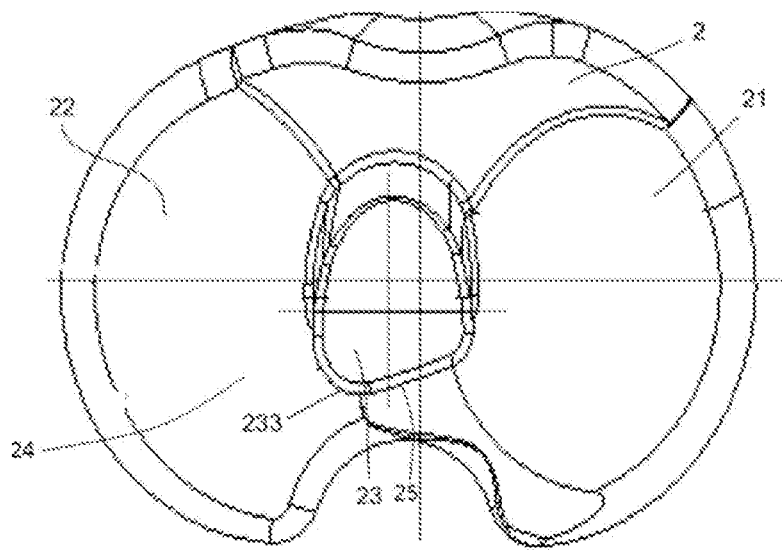
FIG. 2 is a schematic structural view of a tibial component in the artificial knee joint provided by the present disclosure.
Figure 3:
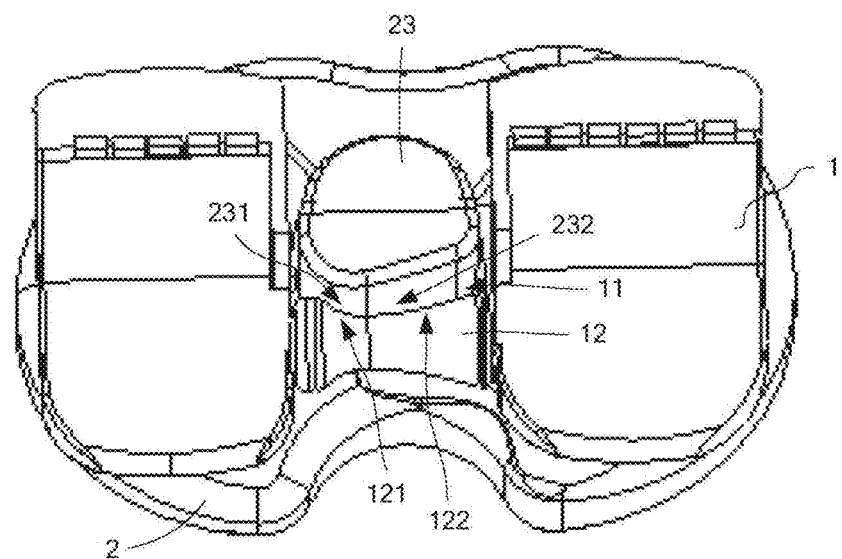
FIG. 3 is a schematic structural view illustrating the use state I of the artificial knee joint provided by the present disclosure.
Figure 4:
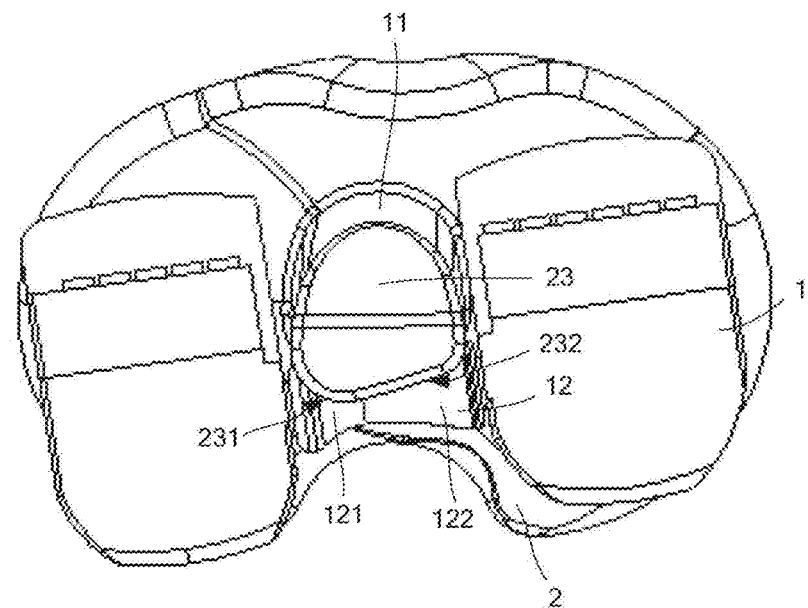
FIG. 4 is a schematic structural view illustrating the use state II of the artificial knee joint provided by the present disclosure.
Figure 5:
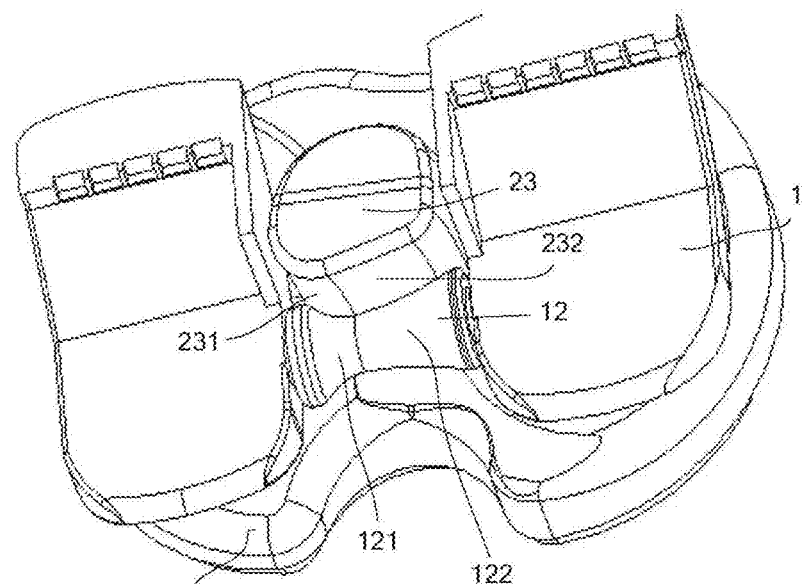
FIG. 5 is a schematic structural view illustrating the use state III of the artificial knee joint provided by the present disclosure.

As shown in FIGS. 1 and 2, the artificial knee joint of the present disclosure comprises a femoral component 1 and a tibial component 2. The femoral component 1 is fixed at a distal femur, and the tibial component 2 is fixed at a proximal end of a tibia. The femoral component 1 and the tibial component 2 cooperate with each other in such a way that the tibia can support the femur through the artificial knee joint according to the present disclosure. Moreover, the femoral component 1 and the tibial component 2 can also cooperate with each other to simulate the flexion and extension of a natural knee FIGS. 3 to 5 illustrate the cooperation relationship between the femoral component 1 and the tibial component 2, in which an half of the anterior part of the femoral component 1 is removed for sake of clearness. As shown in FIGS. 2 and 3, the tibial component 2 includes a medial condyle supporting surface 21 and a lateral condyle supporting surface 22. A post 23 is disposed between the medial condyle supporting surface 21 and the lateral condyle supporting surface 22 of the tibial component 2, and an intercondylar box 11 is provided on the femoral component 1. The post 23 is accommodated in the intercondylar box 11.

Figure 6:
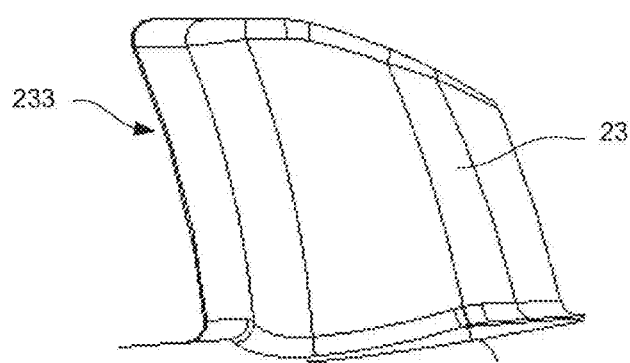
FIG. 6 is a schematic structural view of an post in the artificial knee joint provided by the present disclosure.
Figure 7:
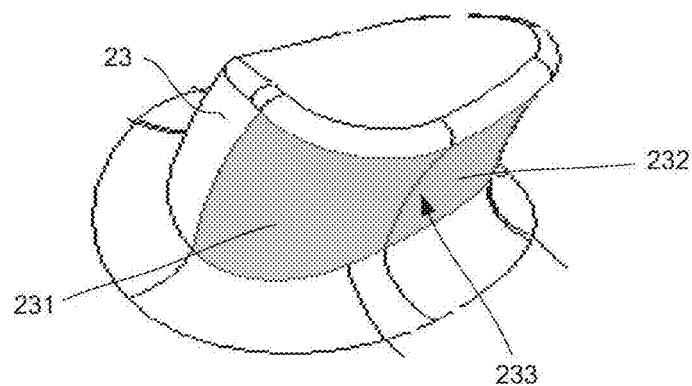
FIG. 7 is a schematic structural perspective view of the post in the artificial knee joint provided by the present disclosure.

As shown in FIGS. 4, 6 and 7, the post 23 is in the shape of a thumb 233 with radian on the whole in side view. The thumb 233 with radian can guarantee that the cam 12 cannot be disengaged from the post 23 (namely dislocation) when the artificial knee joint of the present disclosure performs a high flexion, and hence the safety in utilization of the artificial knee joint of the present disclosure can be guaranteed.

Both an anterior portion and a posterior portion of the post 23 have arc surfaces with smooth transition. A width of the anterior portion of the post 23 in the horizontal axis direction is smaller than that of the posterior portion. Further, part of the anterior portion according to the present disclosure is cut at the anterior inferior direction from the post 23 to form a lower anterior surface on post 23, so that the anterior surface of the post dose not impinge the patella during high flexion or low patella, and hence the patella can be better protected. Moreover, as an anterior surface of the post 23 is a circular surface, when the post 23 makes contact with a circular anterior surface of the intercondylar box 11 of the femoral component 1, the contact area can be increased and the stress can be reduced.

Figure 8:
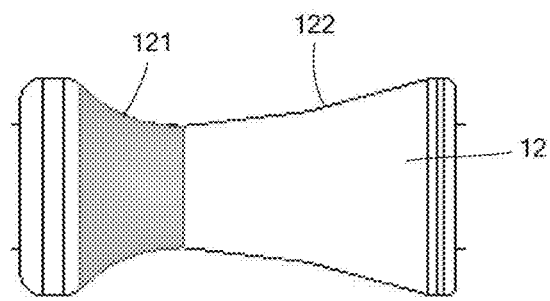
FIG. 8 is a schematic structural perspective view of a cam in the artificial knee joint provided by the present disclosure.

A cam 12 is disposed at the posterior of the intercondylar box 11. As shown in FIG. 8, the cam 12 has a structure in which both ends are large and the central section is small. The largest diameters of the two ends of the cam 12 are preferably equal to each other and may also be unequal. No matter in which case, the implementation of the technical solution of the present disclosure cannot be affected.

As shown in FIGS. 3 to 8, in view of the cross section, a first arc surface 231 is formed on the posterior-lateral surface of the post 23; correspondingly, a third arc surface 121 cooperating with the first arc surface 231 is formed on the anterior-lateral surface of the cam 12. The first arc surface 231 and the third arc surface 121 may be elliptical surfaces or circular surfaces. A curvature of the first arc surface 231 should be approximately equal to, and most preferably equal to, that of the third arc surface 121. In the embodiment, both the first arc surface 231 and the third arc surface 121 are circular surfaces, and have the same curvature radius of 3 to 10 mm and, most preferably, 5 mm.

As shown in FIGS. 3 to 8, in view of the cross section, a second arc surface 232 is formed on the posterior-medial surface of the post 23, disposed on the -medial side of the first arc surface 231. Correspondingly, a fourth arc surface 122 cooperating with the second arc surface 232 is formed on the anterior-medial side the cam 12. The second arc surface 232 and the fourth arc surface 122 may be elliptical surfaces or circular surfaces; and curvatures of the second arc surface 232 and the fourth arc surface 122 should be proximal and, most preferably, equal. In the embodiment, both the second arc surface 232 and the fourth arc surface 122 are circular surfaces, and have the same curvature radius of 30 to 50 mm and, most preferably, 40 mm.

In the present disclosure, in view of the cross section, the curvatures of the second arc surface 232 and the fourth arc surface 122 are preferably smaller than those of the first arc surface 231 and the third arc surface 121, namely the second arc surface 232 and the fourth arc surface 122 are more smooth than the first arc surface 231 and the third arc surface 121. Therefore, the external rotation of the femur relative to the tibia can be better constrained.

When the artificial knee joint provided by the present disclosure is applied to the human body, the cooperation between the femoral component 1 and the tibial component 2 is described as follows.

Dynamic kinematics in the knee of the present disclosure shows a medical pivot motion during flexion and extension. When the knee joint is flexed and extended, the post 23 of the tibial component 2 moves in the intercondylar box 11 of the femoral component 1. The post 23 on the tibial component 2 will contact with the cam 12 on the femoral component 1 only when the knee joint is flexed to a certain angle.

When the post 23 contacts with the cam 12, the first arc surface 231 of the post 23 engages with the third arc surface 121 of the cam 12 at first. The two arc surfaces cooperate with each other to guide the external rotation of the femur relative to the tibia, so as to simulate the external rotation of the femur relative to the tibia when the natural knee is flexed and extended.

As the flexion continues, the second arc surface 232 of the post 23 gradually engages with the fourth arc surface 122 of the cam 12. The two arc surfaces 232 and 122 cooperate with each other to gradually constrain the external rotation of the femur relative to the tibia. Moreover, when the two arc surfaces completely engage with each other, the external rotation of the femur relative to the tibia can be completely constrained.

Figure 9:
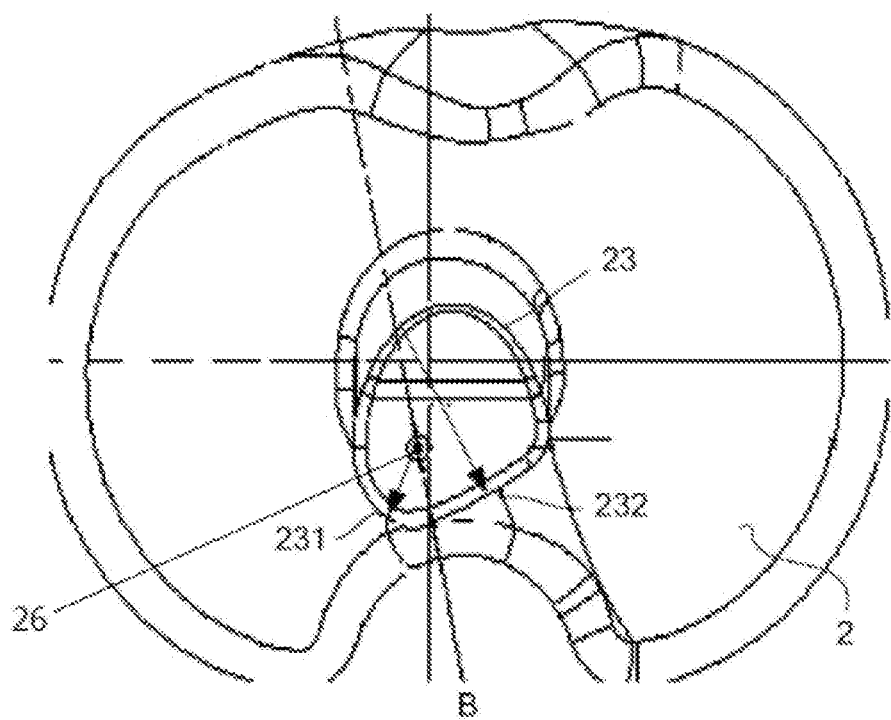
FIG. 9 is a schematic diagram illustrating a first arc surface interfacing with a second arc surface of the upright post in the artificial knee joint provided by the present disclosure.

As shown in FIG. 9, the post 23 is disposed on the tibial component 2. The first arc surface 231 interfaces with the second arc surface 232 preferably on the left posterior side of the post 23; in the cross section of the tibial component 2, a line, which connects the center 26 of the first arc surface 231 and the intersection of the first and second arc surfaces 231 and 232, forms an angle with the posterior-anterior axis of the tibia, that ranges from 5 to 20 degrees and typically from 10 to 15 degrees. This angle is the angle of external rotation of the femur relative to the tibia during the flexion and extension.

As shown in FIG. 2, the center of the post 23 deviates from the center of the tibial component 2, and the post 23 is disposed on a posterior-lateral portion 24 of the tibial component 2, towards to the lateral condyle supporting surface 22. The centers of the two cross-lines in FIG. 2 depict the centers of the post and the tibial component 2, respectively. Further, the center of the post 23 posteriorly deviates 0.5 to 5 mm from the center of the tibial component 2, and laterally deviates 0.5 to 5 mm from the center of the tibial component 2. The eccentricity may be determined by different conditions of the human bodies. The design according to the present disclosure is closer to the anatomy of the human body and is more advantageous to guide and constrain the external rotation of the femur relative to the tibia.

Moreover, the shapes of the post 32 and the cam according to the present disclosure may be symmetrical, and preferably are asymmetrical, because the asymmetrical structures can more easily satisfy the above functional requirements. The posterior surface 25 of the post 23 may be asymmetrical and preferably rotate externally relative to a vertical plane of the bottom of the tibial component. Meanwhile, the anterior surface of the post 23 may also be asymmetrical. In the present disclosure, the post 23 preferably has an asymmetrical structure on the whole. Correspondingly, the cam 12 may only has an asymmetrical anterior surface, but preferably, the cam 12 has an asymmetrical structure on the whole.

The artificial knee joint provided by the present disclosure has advantages below: compared with the prior art, as the first arc surface 231 on the post 23 and the third arc surface 121 on the earn 12 cooperate with each other, smooth external rotation of the femur relative to the tibia can be conveniently guided; as the second arc surface 232 on the post 23 and the fourth arc surface 122 on the cam 12 cooperate with each other, the external rotation of the femur relative to the tibia can be gradually constrained; and when the second arc surface 232 makes full contact with the fourth arc surface 122, the external rotation of the femur relative to the tibia can be completely constrained. The artificial knee joint of the present disclosure adopts an actual means to accurately simulate the flexion and extension of the knee joint, is safe and reliable, can further improve the usage level of the artificial knee joint, satisfies higher requirements of patients, and meanwhile has a higher market value.

The technical solutions of the present disclosure have been described above with reference to the preferred embodiments. It should be understood by those skilled in the art that all the modifications and variations made without departing from the scope and spirit of the present disclosure, disclosed by the appended claims of the present disclosure, should fall within the scope of protection of the appended claims of the present disclosure.

The invention claimed is:

1. An artificial knee joint comprising a femoral component and a tibial component cooperating with each other and configured for application to a femur and the tibia, respectively, wherein:

the femoral component comprises an intercondylar groove, and a cam is disposed at the rear of the intercondylar groove;

the tibial component comprises a medial condyle supporting surface, a lateral condyle supporting surface, and an upright post disposed between the medial condyle supporting surface and the lateral condyle supporting surface and cooperating with the intercondylar groove, the upright post comprises an anterior surface, a posterior surface, a first arc surface formed on a posterior-lateral surface of the upright post, and a second arc surface formed on a posterior-medial surface of the upright post, the second arc surface disposed adjacent a medial side of the first arc surface, the cam comprises a third arc surface formed on an anterior-lateral surface of the cam and a fourth arc surface formed on an anterior-medial surface of the cam, the third arc surface and the fourth arc surface cooperating with the first arc surface and the second arc surface, respectively;

the first arc surface is configured to cooperate with the third arc surface to guide an external rotation of the femur relative to the tibia to simulate the external rotation of the femur relative to the tibia when the natural knee is flexed and extended; and the second arc surface is configured to cooperate with the fourth arc surface to limit the external rotation of the femur relative to the tibia, wherein the upright post is in the shape of a thumb with radian on the whole in side view, wherein the upright post is asymmetrically disposed on the tibial component and is disposed on a posterior-lateral portion of the tibial component, biased towards the lateral condyle supporting surface, wherein the first arc surface, the second arc surface, the third arc surface and the fourth arc surface are all circular or elliptical surfaces, wherein in a cross section view of the tibial component, the curvature of the first arc surface is the same as that of the third arc surface; the curvature of the second arc surface is the same as that of the fourth arc surface; and the curvature of the second arc surface and the fourth arc surface is smaller than that of the first arc surface and the third arc surface, and wherein in a cross section view of the tibial component, an included angle between a straight line, which connects a center of the first arc surface and a juncture of the first and second arc surfaces, and a straight line extending along a posterior-anterior axis of the tibial component, is 5 to 20 degrees.

2. The artificial knee joint according to claim 1, wherein the radius of the first arc surface and the third arc surface is 3 mm to 10 mm; and the radius of the second arc surface and the fourth arc surface is 30 mm to 50 mm.

3. The artificial knee joint according to claim 1, wherein both the upright post and the cam are structurally asymmetrical.

4. The artificial knee joint according to claim 3, wherein the posterior surface of the upright post rotates externally relative to a vertical plane of the bottom of the tibial component.

5. The artificial knee joint according to claim 3, wherein outer edges at both ends of the cam are equal in diameter.

\* \* \* \* \*